United States Patent
Dakka et al.

(10) Patent No.: US 8,247,627 B2
(45) Date of Patent: Aug. 21, 2012

(54) PROCESS FOR PRODUCING PHENOL AND/OR CYCLOHEXANONE

(75) Inventors: Jihad M. Dakka, Whitehouse Station, NJ (US); J. Scott Buchanan, Lambertville, NJ (US); Jane C. Cheng, Bridgewater, NJ (US); Tan-Jen Chen, Kingwood, TX (US); Lorenzo C. DeCaul, Langhorne, PA (US); Terry E. Helton, Bethlehem, PA (US); Jon E. Stanat, Westhampton Beach, NY (US); Francisco M. Benitez, Houston, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 143 days.

(21) Appl. No.: 12/933,935

(22) PCT Filed: Mar. 16, 2009

(86) PCT No.: PCT/US2009/037223
§ 371 (c)(1),
(2), (4) Date: Nov. 2, 2010

(87) PCT Pub. No.: WO2009/131769
PCT Pub. Date: Oct. 29, 2009

(65) Prior Publication Data
US 2011/0037022 A1 Feb. 17, 2011

Related U.S. Application Data

(60) Provisional application No. 61/047,821, filed on Apr. 25, 2008.

(51) Int. Cl.
*C06C 2/68* (2006.01)
*C07C 5/327* (2006.01)
*C07C 45/27* (2006.01)
*C07C 27/08* (2006.01)

(52) U.S. Cl. ........ 585/323; 585/446; 585/467; 585/440; 568/361; 568/798

(58) Field of Classification Search ............... 585/467, 585/446, 440, 323; 568/361, 798
See application file for complete search history.

(56) References Cited

U.S. PATENT DOCUMENTS

| 3,308,069 A | 3/1967 | Wadlinger et al. |
| 3,412,165 A | 11/1968 | Slaugh et al. |
| 3,761,428 A | 9/1973 | Sugier et al. |

(Continued)

FOREIGN PATENT DOCUMENTS

| CS | 177505 | 7/1977 |

(Continued)

OTHER PUBLICATIONS

Du et al., "*The Chemistry of Selective Ring-Opening Catalysts*", Applied Catalysis A: General, 2005, vol. 294, No. 1, pp. 1-21.
Galperin et al., "*Effect of Support Acid-Basic Properties on Activity and Selectivity of Pt Catalysts in Reaction of Methylcyclopentane Ring Opening*", Applied Catalysis A: General, 2003, vol. 239, No. 1-2, pp. 297-304.

(Continued)

*Primary Examiner* — Thuan Dinh Dang
(74) *Attorney, Agent, or Firm* — Anthony G. Boone; Jamie L. Sullivan (57) ABSTRACT

In a process for producing phenol and/or cyclohexanone, benzene and hydrogen are contacted with a first catalyst in a hydroalkylation step to produce a first effluent stream comprising cyclohexylbenzene, cyclohexane, and unreacted benzene. At least part of the first effluent stream is supplied to a first separation system to divide the first effluent stream part into a cyclohexylbenzene-rich stream and a C6 product stream comprising unreacted benzene and cyclohexane.

17 Claims, 2 Drawing Sheets

U.S. PATENT DOCUMENTS

| | | | |
|---|---|---|---|
| RE28,341 | E | 2/1975 | Wadlinger et al. |
| 3,962,362 | A | 6/1976 | Suggitt |
| 4,055,512 | A | 10/1977 | Kageyama et al. |
| 4,094,918 | A | 6/1978 | Murtha et al. |
| 4,122,125 | A | 10/1978 | Murtha et al. |
| 4,147,726 | A | 4/1979 | Wu |
| 4,177,165 | A | 12/1979 | Murtha et al. |
| 4,206,082 | A | 6/1980 | Murtha et al. |
| 4,501,926 | A | 2/1985 | LaPierre et al. |
| 4,891,458 | A | 1/1990 | Innes et al. |
| 5,053,571 | A | 10/1991 | Makkee |
| 5,811,624 | A | 9/1998 | Hantzer et al. |
| 5,906,729 | A | 5/1999 | Chou |
| 6,037,513 | A | 3/2000 | Chang et al. |
| 6,489,529 | B1 | 12/2002 | Cheng et al. |
| 7,563,358 | B2 | 7/2009 | Stavens et al. |
| 7,579,511 | B1 | 8/2009 | Dakka et al. |
| 7,605,107 | B2 | 10/2009 | Soled et al. |
| 2003/0083527 | A1 | 5/2003 | Kuhnle et al. |
| 2006/0166809 | A1 | 7/2006 | Malek et al. |

FOREIGN PATENT DOCUMENTS

| | | |
|---|---|---|
| EP | 0 323 192 | 7/1989 |
| EP | 0 338 734 | 10/1989 |
| GB | 720 064 | 12/1954 |
| GB | 1 454 717 | 11/1976 |
| JP | 54-099788 | 8/1979 |
| JP | 60-204370 | 10/1985 |
| WO | 2009/131769 | 10/2009 |
| WO | 2010/042261 | 4/2010 |

OTHER PUBLICATIONS

Smirniotis et al., "*Comparison Between Zeolite β and γ-Al$_2$O$_3$ Supported PT for Reforming Reactions*", Journal of Catalysis, 1993, vol. 140, pp. 526-542.

Smirniotis et al., "*Increased Aromatization in the Reforming of Mixtures of N-Hexane, Methylcyclopentane and Methylcyclohexane Over Composites of Pt/BaKL Zeolite with Pt/beta or Pt/USY Zeolites*", Applied Catalysis A: General, 1995, vol. 123, No. 1, pp. 59-88.

U.S. Appl. No. 61/155,733, filed Feb. 26, 2009 entitled "Process for Producing Cyclohexylbenzene".

Borodina, I.B. et al., "*Hydroalkylation of Benzene and Ethylbenzene Over Metal Containing Zeolite Catalysts*", Microporous and Mesoporous Materials, 2007, vol. 105, No. 1-2, pp. 181-188.

Gault, F.G. "*Mechanisms of Skeletal Isomerization of Hydrocarbons on Metals*" Advances in Catalysis, 1981, vol. 30, pp. 1-95.

Gonzales-Cortes, S.L. et al., "*Tuning the Ring-Opening Reaction of 1,3-dimethylcyclohexane with the Addition of Potassium Over Ir-Containing Catalysts*" Chemical Engineering Journal, 2008, vol. 139, pp. 147-156.

Koel, B.E. et al., "*Thermochemistry of the Selective Dehydrogenation of Cyclohexane to Benzene on Pt Surfaces*", Journal of Molecular Catalysis: A Chemical, 1998, vol. 131, pp. 39-53.

Soled, S.L. et al. "*Supported Metal Catalysts: Some Interesting New Leads in an Old Field*" Scientific Bases for the Preparation of Heterogeneous Catalysts, 2006, vol. 162, pp. 103-110.

Neftekhimiya, V17 N. 5705-9, Spet-Oct. 1977, "A Commerical Synthesis of Phenylcyclohexane ((PHCH)) by the Hydrodimerization of Benzene".

PROCESS FOR PRODUCING PHENOL AND/OR CYCLOHEXANONE

CROSS REFERENCE TO RELATED PATENT APPLICATIONS

This application is a national stage filing of International Patent Cooperation Treaty Application No. PCT/US2009/037223, filed Mar. 16, 2009, which claims priority from U.S. Ser. No. 61/047,821, filed Apr. 25, 2008, the disclosure of which is fully incorporated herein by reference.

FIELD

The present invention relates to a process for producing phenol and/or cyclohexanone.

BACKGROUND

Phenol is an important product in the chemical industry and is useful in, for example, the production of phenolic resins, bisphenol A, ε-caprolactam, adipic acid, and plasticizers.

Currently, the most common route for the production of phenol is the Hock process. This is a three-step process in which the first step involves alkylation of benzene with propylene to produce cumene, followed by oxidation of the cumene to the corresponding hydroperoxide and then cleavage of the hydroperoxide to produce equimolar amounts of phenol and acetone. However, world demand for phenol is growing more rapidly than that for acetone. In addition, the cost of propylene is likely to increase, due to a developing shortage of propylene. Thus, a process that uses higher alkenes instead of propylene as feed and coproduces higher ketones, rather than acetone, may be an attractive alternative route to the production of phenols.

For example, oxidation of cyclohexylbenzene (analogous to cumene oxidation) could offer an alternative route for phenol production without the problem of acetone co-production. This alternative route co-produces cyclohexanone, which has a growing market and is used as an industrial solvent, as an activator in oxidation reactions and in the production of adipic acid, cyclohexanone resins, cyclohexanone oxime, caprolactam and nylon 6. Moreover, cyclohexanone and phenol are readily interconverted by dehydrogenation and hydrogenation, respectively, so that the cyclohexylbenzene route offers the potential not only for producing a mixture of phenol and cyclohexanone but also for maximizing the production of phenol or cyclohexanone according to market demand.

It is well known cyclohexylbenzene can be produced from benzene by the process of hydroalkylation or reductive alkylation. In this process, benzene is heated with hydrogen in the presence of a catalyst such that the benzene undergoes partial hydrogenation to produce cyclohexene which then alkylates the benzene starting material. An example of such a process is described in U.S. Pat. No. 6,037,513.

However, despite its potential advantages, no commercial process for manufacture of phenol and/or cyclohexanone via the hydroalkylation of benzene and the oxidation and cleavage of the resultant cyclohexylbenzene, has yet been developed. Among the problems that need to be addressed in a commercial process are the relatively low conversion rate in the hydroalkylation step and the tendency for the hydroalkylation to generate significant quantities of by-products, such as cyclohexane. The present invention seeks to provide an efficient and economical cyclohexylbenzene-based process for the production of phenol and/or cyclohexanone from benzene, in which the problems inherent in the commercial application of the process are alleviated.

SUMMARY

In one aspect, the invention resides in a process for producing phenol and/or cyclohexanone, the process comprising:

(a) contacting benzene and hydrogen with a first catalyst under hydroalkylation conditions to produce a first effluent stream comprising cyclohexylbenzene, cyclohexane, and unreacted benzene;

(b) supplying said first effluent stream to a first separation system to divide said first effluent stream into a cyclohexylbenzene-rich stream and a C6 product stream comprising cyclohexane and benzene;

(c) contacting at least part of said C6 product stream with a second catalyst under dehydrogenation conditions to convert at least part of the cyclohexane to benzene and produce a second effluent stream comprising benzene and hydrogen;

(d) recycling at least part of the second effluent stream to said contacting (a);

(e) contacting at least part of said cyclohexylbenzene-rich stream with an oxygen-containing gas in the presence of a third catalyst under oxidation conditions to oxidize the cyclohexylbenzene in said cyclohexylbenzene-rich stream to produce cyclohexylbenzene hydroperoxide; and (f) converting cyclohexylbenzene hydroperoxide from (e) to produce phenol and cyclohexanone.

Conveniently, the process alternatively comprises (g) dividing said C6 product stream in said supplying (b) into a cyclohexane-rich stream, and a benzene-rich stream;

(h) recycling the benzene-rich stream to said contacting (a); and (i) contacting the cyclohexane-rich stream with a second catalyst in said contacting (c).

Conveniently, fresh benzene supplied to the process contains less than 5 ppm by weight sulfur, less than 1 ppm by weight nitrogen and less than 500 ppm by weight water. In one embodiment, fresh benzene is supplied to said first separation system.

Conveniently, fresh hydrogen supplied to the process contains less than 5 ppm by weight hydrogen sulfide, less than 1 ppm by weight nitrogen and less than 5 ppm by weight carbon monoxide. In one embodiment, fresh hydrogen is supplied to said contacting (d).

Conveniently, the first catalyst comprises a molecular sieve and a hydrogenation metal. In one embodiment, the molecular sieve of said first catalyst is selected from zeolite beta, zeolite X, zeolite Y, a MCM-22 family molecular sieve and mixtures thereof and the hydrogenation metal of said first catalyst is selected from palladium, ruthenium, nickel, zinc, tin, cobalt and mixtures thereof.

Conveniently, at least 50 wt % of said hydrogenation metal is supported on an inorganic oxide different from said molecular sieve and generally comprising an oxide of at least one element of Groups 2, 4, 13 and 14 of the Periodic Table of Elements.

Conveniently, said hydroalkylation conditions include a temperature of about 50 to about 400° C., a pressure of about 100 to about 7000 kPa, a weight hourly space velocity of about 0.01 to about 100 hr$^{-1}$ and a benzene to hydrogen molar ratio of about 0.01 to about 100.

In one embodiment, the process further comprises dividing said first effluent stream into at least first and second portions;

cooling the first portion of said first effluent stream; and recycling said cooled first effluent stream portion to said contacting (a).

Conveniently, said first separation system further separates a dicyclohexylbenzene-rich stream from said first effluent stream and the process further comprises contacting said dicyclohexylbenzene-rich stream with further benzene in the presence of a transalkylation catalyst to convert said dicyclohexylbenzene to additional cyclohexylbenzene.

Typically, second catalyst comprises a metal or compound thereof of Group 8 of the Periodic Table on a porous, non-acidic support and said dehydrogenation conditions comprise a temperature between about 330° C. and about 500° C. and a pressure between about 100 and about 1000 kPa.

Conveniently, said third catalyst comprises a cyclic imide of the general formula (I):

wherein each of $R^1$ and $R^2$ is independently selected from hydrocarbyl and substituted hydrocarbyl radicals having 1 to 20 carbon atoms, or from the groups $SO_3H$, $NH_2$, OH, and $NO_2$ or from the atoms H, F, Cl, Br, and I, provided that $R^1$ and $R^2$ can be linked to one another via a covalent bond;

each of $Q^1$ and $Q^2$ is independently selected from C, CH, $CR^3$;

each of X and Z is independently selected from C, S, $CH_2$, N, P and elements of Group 4 of the Periodic Table;

Y is O or OH;

k is 0, 1, or 2;

l is 0, 1, or 2;

m is 1 to 3.

In one embodiment, the cyclic imide comprises N-hydroxyphthalimide and is dissolved in said at least part of said cyclohexylbenzene-rich stream prior to said contacting (f).

In one embodiment, said converting (g) is effected in at least two stages comprising a first stage conducted at a temperature of less than 50° C. and a second stage conducted at a temperature greater than the first stage temperature but less than 150° C. Conveniently, said converting (g) further comprises a third stage conducted at a temperature of about 120° C. to about 150° C.

Conveniently, said converting (g) comprises contacting said cyclohexylbenzene hydroperoxide with a fourth catalyst, such as sulfuric acid.

DETAILED DESCRIPTION OF THE EMBODIMENTS

Described herein is a process for producing phenol and/or cyclohexanone from benzene and hydrogen in which the various steps of the process, particularly hydroalkylation, oxidation, cleavage and product recovery, are performed and integrated in a manner that maximizes the utilization of the feedstocks and the yield of the desired products and minimizes by-product formation.

Feed Pretreatment

Any commercially available benzene and hydrogen feedstocks can be used in the present process. However, in hydroalkylation, it is desirable for the feedstocks to be as pure as possible. The sulfur, nitrogen, water, carbon monoxide and/or other impurities in the benzene feed and hydrogen feed may be removed by adsorption using 13X, 4A, Selexsorb CD, clay, Zn, Cu, and or any other effective adsorbents. The preferred sulfur level in the benzene feed to the hydroalkylation catalyst is less 5 wppm, generally less than 1 wppm. The preferred water level in the benzene feed is less than 500 wppm, generally less than 250 wppm. The preferred nitrogen level in the benzene feed is less than 1 wppm. Similarly, the preferred hydrogen sulfide level in the hydrogen feed is less than 5 wppm, generally less than 1 wppm. The preferred CO level in the hydrogen feed is also less than 5 wppm, generally less than 1 wppm. The preferred nitrogen level in the hydrogen feed is less than 1 wppm.

Production of Cyclohexylbenzene

In the present process, cyclohexylbenzene is produced by contacting benzene with hydrogen under hydroalkylation conditions in the presence of a hydroalkylation catalyst whereby the benzene undergoes the following reaction (1) to produce cyclohexylbenzene (CHB):

The hydroalkylation reaction can be conducted in a wide range of reactor configurations including fixed bed, slurry reactors, and/or catalytic distillation towers. In addition, the hydroalkylation reaction can be conducted in a single reaction zone or in a plurality of reaction zones, in which at least the hydrogen is introduced to the reaction in stages. Suitable reaction temperatures are between about 50° C. and about 400° C., such as between about 100° C. and about 250° C., while suitable reaction pressures are between about 100 and about 7,000 kPa, such as between about 500 and about 5,000 kPa. Suitable values for the molar ratio of hydrogen to benzene are between about 0.01 and about 100, more particularly between about 0.15:1 and about 15:1, such as between about 0.4:1 and about 4:1, for example between about 0.4 and about 0.9:1. The benzene weight hourly space velocity is normally from about 0.01 to about 100 $hr^{-1}$.

The catalyst employed in the hydroalkylation reaction is a bifunctional catalyst comprising a molecular sieve with an acid function and a hydrogenation metal. Suitable molecular sieves include zeolite beta, zeolite X, zeolite Y and molecular sieves of the MCM-22 family The term "MCM-22 family material" (or "material of the MCM-22 family" or "molecular sieve of the MCM-22 family"), as used herein, includes one or more of:

molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types", Fifth edition, 2001, the entire content of which is incorporated as reference);

molecular sieves made from a common second degree building block, being a 2-dimensional tiling of such MWW framework topology unit cells, forming a monolayer of one unit cell thickness, preferably one c-unit cell thickness;

molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and molecular sieves made by any regular or random 2-dimensional or 3-dimensional combination of unit cells having the MWW framework topology.

Molecular sieves of MCM-22 family generally have an X-ray diffraction pattern including d-spacing maxima at 12.4±0.25, 6.9±0.15, 3.57±0.07 and 3.42±0.07 Angstrom. The X-ray diffraction data used to characterize the material (b) are obtained by standard techniques using the K-alpha doublet of copper as the incident radiation and a diffractometer equipped with a scintillation counter and associated computer as the collection system. Molecular sieves of MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), MCM-36 (described in U.S. Pat. No. 5,250,277), MCM-49 (described in U.S. Pat. No. 5,236,575), MCM-56 (described in U.S. Pat. No. 5,362,697), UZM-8 (described in U.S. Pat. No. 6,756,030), and mixtures thereof. Preferably, the molecular sieve is selected from (a) MCM-49, (b) MCM-56 and (c) isotypes of MCM-49 and MCM-56, such as ITQ-2.

Any known hydrogenation metal can be employed in the hydroalkylation catalyst although suitable metals include palladium, ruthenium, nickel, zinc, tin, and cobalt, with palladium being particularly advantageous. Generally, the amount of hydrogenation metal present in the catalyst is between about 0.05 and about 10 wt %, such as between about 0.1 and about 5 wt %, of the catalyst. In one embodiment, where the molecular sieve is an aluminosilicate, the amount of hydrogenation metal present is such that the molar ratio of the aluminum in the molecular sieve to the hydrogenation metal is from about 1.5 to about 1500, for example from about 75 to about 750, such as from about 100 to about 300.

The hydrogenation metal may be directly supported on the molecular sieve by, for example, impregnation or ion exchange. However, in a more preferred embodiment, at least 50 wt %, for example at least 75 wt %, and generally substantially all of the hydrogenation metal is supported on an inorganic oxide separate from but composited with the molecular sieve. In particular, it is found that by supporting the hydrogenation metal on the inorganic oxide, the activity of the catalyst and its selectivity to cyclohexylbenzene and dicyclohexylbenzene are increased as compared with an equivalent catalyst in which the hydrogenation metal is supported on the molecular sieve.

The inorganic oxide employed in such a composite hydroalkylation catalyst is not narrowly defined provided it is stable and inert under the conditions of the hydroalkylation reaction. Suitable inorganic oxides include oxides of Groups 2, 4, 13 and 14 of the Periodic Table of Elements, such as alumina, titania, and/or zirconia. As used herein, the numbering scheme for the Periodic Table Groups is as disclosed in Chemical and Engineering News, 63(5), 27 (1985).

The hydrogenation metal is deposited on the inorganic oxide, conveniently by impregnation, before the metal-containing inorganic oxide is composited with said molecular sieve to produce the catalyst composite. Typically, the catalyst composite is produced by co-pelletization, in which a mixture of the molecular sieve and the metal-containing inorganic oxide are formed into pellets at high pressure (generally about 350 to about 350,000 kPa), or by co-extrusion, in which a slurry of the molecular sieve and the metal-containing inorganic oxide, optionally together with a separate binder, are forced through a die. If necessary, additional hydrogenation metal can subsequently be deposited on the resultant catalyst composite.

Suitable binder materials include synthetic or naturally occurring substances as well as inorganic materials such as clay, silica and/or metal oxides. The latter may be either naturally occurring or in the form of gelatinous precipitates or gels including mixtures of silica and metal oxides. Naturally occurring clays which can be used as a binder include those of the montmorillonite and kaolin families, which families include the subbentonites and the kaolins commonly known as Dixie, McNamee, Georgia and Florida clays or others in which the main mineral constituent is halloysite, kaolinite, dickite, nacrite or anauxite. Such clays can be used in the raw state as originally mined or initially subjected to calcination, acid treatment or chemical modification. Suitable metal oxide binders include silica, alumina, zirconia, titania, silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia.

The hydroalkylation reaction is exothermic, and so the reaction system must take heat management into account. A preferred method is to recycle a portion of the effluent from the hydroalkylation reactor through a cooling heat exchanger, and mix the cooled recycle stream with the feed. It can also be advantageous to have more than one hydroalkylation bed or reactor, and add hydrogen in stages.

Separation of Cyclohexylbenzene

Although the hydroalkylation step is highly selective towards cyclohexylbenzene, in addition to the desired monoalkylated species, the effluent from the hydroalkylation reaction will normally contain some dialkylated and other heavy products, as well as unreacted benzene feed. The hydroalkylation effluent is therefore fed to a separation system normally comprising at least two distillation towers. In the first distillation tower, unreacted benzene feed is recovered from the effluent and recycled to the hydroalkylation reactor. Specifically, in one embodiment, the unreacted benzene is recovered along with the cyclohexane. In other embodiments, a cyclohexane-rich stream is recovered from the first distillation tower independent of a benzene-rich stream. In still another embodiment, the cyclohexane can be substantially separated from the benzene by adding an addi- tional separation step. The substantial separation of cyclohexane from benzene can be done but this alternative approach may be prohibitively expensive depending on the circumstances. The bottoms from the first distillation tower are further distilled to recover a purified cyclohexylbenzene product stream. Materials heavier than cyclohexylbenzene may be removed in a purge stream. Optionally, in this step, a polyalkylate stream, comprising at least di-cyclohexylbenzene, may be recovered for feeding to an optional transalkylation step. A heavies stream is still removed at this step and purged from the process. This heavies stream may be a slipstream of the polyalkylate stream, or may be the residue from the purification of a polyalkylate stream, or a combination of both. Generally, the cyclohexylbenzene recovery is accomplished using one or optionally two vacuum distillation towers.

Transalkylation of Dicyclohexylbenzene

Depending on the amount of dicyclohexylbenzene present in the hydroalkylation effluent, it may be desirable to transalkylate the dicyclohexylbenzene with additional benzene to maximize the production of the desired monoalkylated species. Transalkylation with additional benzene is typically effected in a transalkylation reactor, separate from the hydroalkylation reactor, over a suitable transalkylation catalyst, such as a molecular sieve of the MCM-22 family, zeolite beta, MCM-68 (see U.S. Pat. No. 6,014,018), zeolite Y and mordenite. The transalkylation reaction is typically conducted under at least partial liquid phase conditions, which suitably include a temperature of about 100 to about 300° C., a pressure of about 800 to about 3500 kPa, a weight hourly space velocity of about 1 to about 10 $hr^{-1}$ on total feed, and a benzene/dicyclohexylbenzene weight ratio about of 1:1 to about 5:1.

Cyclohexane Dehydrogenation

In addition the effluent from the hydroalkylation reactor will normally contain significant amounts of cyclohexane, since a competing process to the hydroalkylation of benzene to produce cyclohexylbenzene involves the complete saturation of the benzene to produce cyclohexane according to the following reaction (2):

(2)

Even with highly selective hydroalkylation processes such as that described above, it is common to find levels of cyclohexane between 5 wt % and 20 wt % in the reaction product (ignoring unconverted benzene). Since benzene conversions in the hydroalkylation step are typically only 40-60%, at least a portion of the $C_6$ product fraction is typically recycled. However, cyclohexane cannot be readily separated from benzene by distillation due to their close boiling points. But in one embodiment, cyclohexane can be separated from benzene to some extent by pulling a cyclohexane-rich stream from the separation system conveniently as a slip stream from the first distillation tower. The slip stream would typically be pulled from the first distillation tower somewhere between the feed point and the overhead stream. In other embodiments, cyclohexane can be more substantially separated from the $C_6$ product stream by introducing an additional cyclohexane/benzene separation step into the overall process. In still other embodiments, the $C_6$ product stream is not divided into a cyclohexane-rich stream and benzene-rich stream. With the exception of the substantial separation of the cyclohexane from $C_6$ product stream, however, the cyclohexane will typically tend to build up in the $C_6$ recycle stream in the cyclohexylbenzene synthesis step, where it can displace benzene and also lead to further undesirable byproducts.

Regardless of how the cyclohexane is recovered from the separation system, there are at least three approaches to the dehydrogenation of cyclohexane. First, the undivided $C_6$ product stream comprising benzene and cyclohexane can be fed to the dehydrogenation system. Second, a cyclohexane-rich stream recovered from the separation system as a slip stream can be fed to the dehydrogenation system. Third, a substantially pure cyclohexane stream recovered through subsequent distillation of the C6 product stream can be fed to the dehydrogenation system, however, this third approach may be unduly expensive because of the close boiling points of benzene and cyclohexane.

When a stream is described as being "rich" in a specified species, it is meant that the specified species in that stream is enriched relative to other streams in the same system on a weight percentage basis. For illustration purposes only, a cyclohexane-rich stream leaving the separation system will have a cyclohexane wt % greater than either the feed to the separation system, the benzene-rich stream, or the cyclohexylbenzene-rich stream. A "$C_6$" species generally means any species containing 6 or more carbon atoms.

In the present process, the problem of cyclohexane production is minimized by integrating a dehydrogenation step for the cyclohexane into the recycle loop of the hydroalkylation. Thus, in one embodiment wherein the benzene and cyclohexane are recovered as a C6 product stream, at least a portion of the $C_6$ product stream (typically containing more than 50% benzene and less than 50% cyclohexane) removed from the cyclohexylbenzene product may be fed to a dehydrogenation reactor where the cyclohexane is converted to benzene, with selectivities greater than 90%, such as greater than 96%, for example greater than 99%, according to the following reaction (3):

(3)

In another embodiment, the cyclohexane-rich stream may be fed to a dehydrogenation reactor and then recycled back to the hydroalkylation step.

Reaction (3) is of course the inverse of reaction (2). Thus, whereas reaction (2) is favored by conditions of relatively low temperature and high pressure, to drive reaction (3) in the forward direction, thermodynamics demands lower pressure and/or higher temperatures. Thus the cyclohexane dehydrogenation step is typically run under conditions comprising a temperature greater than 300° C., such as between about 330° C. and about 430° C., and a pressure less than 1000 kPa, such as between about 100 and about 500 kPa.

The cyclohexane dehydrogenation is generally conducted in the presence of a catalyst having an active metal function, such as one or more Group VIII metals on a porous non-acidic support. Suitable Group VIII metals include palladium, platinum, nickel, rhodium, ruthenium and combinations thereof. Conveniently, the dehydrogenation metal is combined with one or more other elements, such as potassium, sodium, tin and/or phosphorus, for acid site neutralization and for improving catalyst stability and selectivity. Suitable supports for the dehydrogenation catalyst include aluminum oxide, silicon oxide, titanium oxide, zirconium oxide, activated carbon and combinations thereof. The support typically has a surface area of more than 3 m$^2$/g, such as about 20 to about 500 m$^2$/g. The cyclohexane conversion is typically greater than 50%, such as from about 70 to about 99%.

A gas co-feed to the dehydrogenation reactor is not required, but a hydrogen gas co-feed is preferred to suppress catalyst coking, typically so that the H$_2$/hydrocarbon molar feed ratio is between about 0.5:1 and about 5:1. In fact, in one embodiment, the fresh make-up hydrogen for the overall process is supplied to the cyclohexane dehydrogenation step. The excess and co-produced hydrogen is then compressed and recycled to the hydroalkylation reactor.

Any known reactor configuration can be employed to effect the cyclohexane dehydrogenation, including fixed bed, moving bed and catalytic distillation reactors. Moreover, the reaction can be conducted as a batch or a continuous process.

Cyclohexylbenzene Oxidation

In order to convert the cyclohexylbenzene into phenol and cyclohexanone, the cyclohexylbenzene is initially oxidized to the corresponding hydroperoxide. This is accomplished by introducing an oxygen-containing gas, such as air, into a liquid phase containing the cyclohexylbenzene. Unlike cumene, atmospheric air oxidation of cyclohexylbenzene in the absence of a catalyst is very slow and hence the oxidation is normally conducted in the presence of a catalyst.

Suitable catalysts for the cyclohexylbenzene oxidation step are cyclic imides of the general formula (I):

(I)

wherein each of R$^1$ and R$^2$ is independently selected from hydrocarbyl and substituted hydrocarbyl radicals having 1 to 20 carbon atoms, or the groups SO$_3$H, NH$_2$, OH and NO$_2$, or the atoms H, F, Cl, Br and I provided that R$^1$ and R$^2$ can be linked to one another via a covalent bond; each of Q$^1$ and Q$^2$ is independently selected from C, CH, CR$^3$; each of X and Z is independently selected from C, S, CH$_2$, N, P and elements of Group 4 of the Periodic Table; Y is O or OH; k is 0, 1, or 2; l is 0, 1, or 2; m is 1 to 3 such as 1, 2 or 3, and R$^3$ can be any of the entities (radicals, groups, or atoms) listed for R$^1$. Conveniently, each of R$^1$ and R$^2$ is independently selected from aliphatic alkoxy or aromatic alkoxy radicals, carboxyl radicals, alkoxy-carbonyl radicals and hydrocarbon radicals, each of which radicals has 1 to 20 carbon atoms.

Generally, the cyclic imide employed as the oxidation catalyst obeys the general formula (II):

(II)

wherein each of R$^7$, R$^8$, R$^9$, and R$^{10}$ is independently selected from hydrocarbyl and substituted hydrocarbyl radicals having 1 to 20 carbon atoms, or the groups SO$_3$H, NH$_2$, OH and NO$_2$, or the atoms H, F, Cl, Br and I; each of X and Z is independently selected from C, S, CH$_2$, N, P and elements of Group 4 of the Periodic Table; Y is O or OH; k is 0, 1, or 2, and l is 0, 1, or 2. Conveniently, each of R$^7$, R$^8$, R$^9$, and R$^{10}$ is independently selected from aliphatic alkoxy or aromatic alkoxy radicals, carboxyl radicals, alkoxy-carbonyl radicals and hydrocarbon radicals, each of which radicals has 1 to 20 carbon atoms.

In one practical embodiment, the cyclic imide catalyst comprises N-hydroxyphthalimide.

These cyclic imide can be used either alone or in the presence of a free radical initiator and can be used as liquid-phase, homogeneous catalysts or can be supported on a solid carrier to provide a heterogeneous catalyst. Typically, the N-hydroxy substituted cyclic imide is employed in an amount between 0.0001 wt % to 15 wt %, such as between 0.001 to 5 wt %, of the cyclohexylbenzene. In one embodiment, the cyclic imide catalyst is added to the oxidation reaction step by dissolving in either the cyclohexylbenzene feed or in the reaction media (or a combination). The catalyst is advantageously added to the reaction media, where the temperature is already high, and where there is present some hydroperoxide, both of which contribute to the improved solubility of the solid catalyst.

Suitable conditions for the oxidation step include a temperature between about 70° C. and about 200° C., such as about 90° C. to about 130° C., and a pressure of about 50 to 10,000 kPa. Any oxygen-containing gas, preferably air, can be used as the oxidizing medium. The reaction can take place in batch reactors or continuous flow reactors. A basic buffering agent may be added to react with acidic by-products that may form during the oxidation. In addition, an aqueous phase may be introduced, which can help dissolve basic compounds, such as sodium carbonate.

The products of the oxidation step are a liquid effluent containing cyclohexylbenzene hydroperoxide and unreacted cyclohexylbenzene and a flue gas composed mainly of oxygen-depleted air. The cyclohexylbenzene hydroperoxide may be concentrated by stripping off at least a portion of the unreacted cyclohexylbenzene in one or more vacuum flash/distillation steps. Preferably, the cyclohexylbenzene hydroperoxide is not concentrated, and is used in its dilute form for the subsequent cleavage step. The unconverted cyclohexylbenzene in this stream is recovered after the cleavage section, and is recycled to the oxidation section.

The flue gas is cooled, and at least a portion of the vapor products are condensed and separated from non-condensable gas. Preferably, an adsorbent bed (e.g. of activated carbon) is used to recover further organic compounds from the flue gas.

Hydroperoxide Cleavage

The final reactive step in the conversion of the cyclohexylbenzene into phenol and cyclohexanone involves cleavage of the cyclohexylbenzene hydroperoxide, which is conveniently effected by contacting the hydroperoxide with a catalyst in the liquid phase at a temperature of about 20° C. to about 150° C., such as about 40° C. to about 120° C., for example about 60° C. to about 100° C., and a pressure of about 50 to about 2,500 kPa, such as about 100 to about 1000 kPa for example about 100 to about 200 kPa. Typical residence times are of the order of 5 to 10 minutes. The cyclohexylbenzene hydroperoxide may be diluted with an organic solvent inert to the cleavage reaction, such as methyl ethyl ketone, cyclohexanone, phenol or cyclohexylbenzene, to assist in heat removal.

The cleavage reaction is conveniently conducted in a least two stages. The first reaction stage is operated at relatively mild conditions; lower temperature (less than 50° C.) and lower acid concentrations, so that phenylcyclohexanols in the feed do not get dehydrated to olefins. Because of the mild conditions, the first reaction stage can operate with a higher level of cyclohexylbenzene hydroperoxide with a residence time preferably around 5-10 minutes. The first reaction stage is conveniently conducted in a fixed bed or continuous stirred reactor.

In a second reaction step, the cyclohexylbenzene hydroperoxide content is reduced to about 0.5% in a plug flow reactor with preferably about 30 sec residence time. This reactor can simply be a piece of uninsulated interconnecting pipe. In a third reaction step, the reaction mixture is quickly heated to 120-150° C. This heated mixture flows through another piece of pipe with preferably about 30 sec residence time with plug flow, and is then quickly cooled. This last, high severity step converts the phenylcyclohexanols to phenylcyclohexenes. The short residence time does not give the phenylcyclohexenes time to react/condense with other components, thus resulting in reduced phenol tar formation.

The catalyst employed in the cleavage step can be a homogeneous catalyst or a heterogeneous catalyst.

Suitable homogeneous cleavage catalysts include sulfuric acid, perchloric acid, phosphoric acid, hydrochloric acid and p-toluenesulfonic acid. Ferric chloride, boron trifluoride, sulfur dioxide and sulfur trioxide are also effective homogeneous cleavage catalysts. The preferred homogeneous cleavage catalyst is sulfuric acid, with preferred concentrations in the range of 0.05 to 0.5 wt %. For a homogeneous acid catalyst, a neutralization step normally follows the cleavage step. Such a neutralization step typically involves contact with a basic component, such as sodium phenylate, with subsequent settling and decanting for removal a salt-enriched aqueous phase.

Suitable heterogeneous catalysts for use in the cleavage of cyclohexylbenzene hydroperoxide include smectite clays, such as an acidic montmorillonite silica-alumina clay, as described in U.S. Pat. No. 4,870,217, acidic ion-exchange resins (e.g., Amberlyst 15), acidic mixture of metal oxides (WO$_3$/ZrO$_2$, MoO$_3$/ZrO$_2$, etc.), and aluminum chloride.

Treatment of Cleavage Effluent

The effluent from the cleavage reaction comprises phenol and cyclohexanone in substantially equimolar amounts, together with unreacted cyclohexylbenzene. The effluent is therefore subjected to one or more separation steps at least to remove the unreacted cyclohexylbenzene for recycle to the oxidation step, and normally to recover the phenol and cyclohexanone as separate products. Since cyclohexanone and phenol produce an azeotropic mixture composed of 28 wt % cyclohexanone and 72 wt % phenol, the latter separation normally involves vacuum or extractive distillation.

Depending on the market demand for phenol, some or all of the cyclohexanone in the cleavage effluent, with or without prior removal of the phenol, can be dehydrogenated to produce additional phenol according to the reaction (4):

Any suitable dehydrogenation catalyst can be used in reaction (4), such as, for example, the promoted nickel catalysts described in U.S. Pat. No. 4,417,076. Suitable conditions for the dehydrogenation step comprise a temperature of about 250° C. to about 500° C. and a pressure of about 0.01 atm to about 20 atm (1 kPa to 2000 kPa), such as a temperature of about 300° C. to about 450° C. and a pressure of about 1 atm to about 3 atm (100 kPa to 300 kPa).

Alternatively, if cyclohexanone is in higher demand, some or all of the phenol in the cleavage effluent, with or without prior removal of the cyclohexanone, can be hydrogenated to produce additional cyclohexanone according to the inverse of reaction (4). Any suitable hydrogenation catalyst can be used in this reaction, such as, for example, a platinum or palladium catalyst. Similarly the hydrogenation conditions are not closely controlled and typically comprise a temperature of about 20° C. to about 250° C., a pressure of about 101 kPa to about 10,000 kPa, and a hydrogen to phenol molar ratio of about 1:1 to about 100:1. The hydrogenation reaction can be conducted in a wide range of reactor configurations including fixed bed, slurry reactors, and/or catalytic distillation towers. Depending on the conditions employed in the hydrogenation process, some or all of the cyclohexanone may be further reduced to cyclohexanol.

The phenol produced by the present process can be used in, for example, the production of bisphenol-A, whereas cyclohexanone and mixtures of cyclohexanone and cyclohexanol are useful feedstocks for the production of nylon 6 and nylon 6,6.

One example of a process according to the present invention will now be described with reference to the accompanying drawings.

Figure 1:
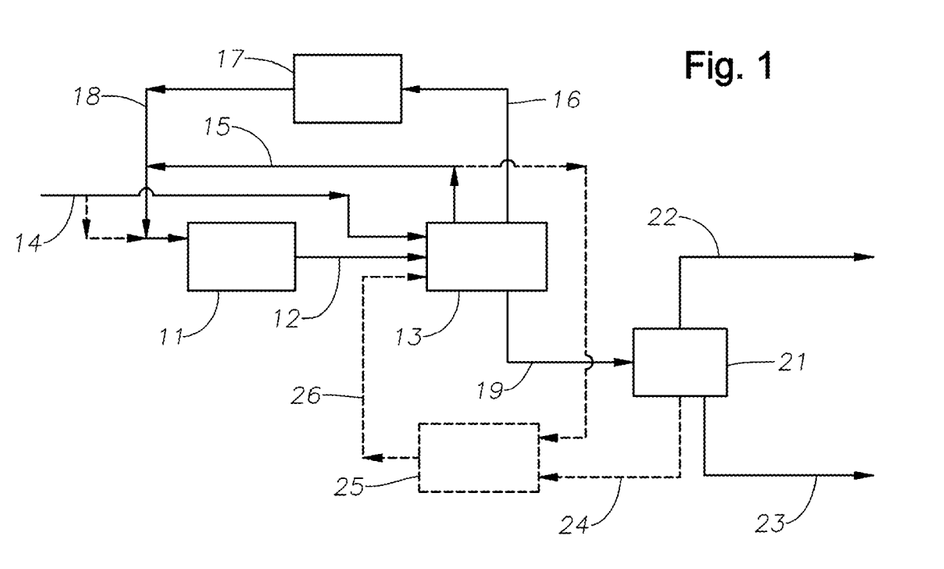
FIG. 1 is a flow diagram of the cyclohexylbenzene synthesis step of a process according to one example of the invention.

Referring to FIG. 1, which is a flow diagram of the cyclohexylbenzene synthesis step of a preferred embodiment of the present process, benzene and hydrogen are supplied to a hydroalkylation reactor 11, where they react to produce cyclohexylbenzene, together with some cyclohexane and dicyclohexylbenzene. The effluent 12 from the hydroalkylation reactor 11 is fed to a first distillation unit 13, which also receives fresh make-up benzene 14. A first benzene-rich overhead stream 15 is removed from the first distillation unit 13 and recycled to the hydroalkylation reactor 11, while a second overhead stream 16 (i.e. a cyclohexane-rich slip stream) rich in cyclohexane is removed from the first distillation unit 13 and fed to a dehydrogenation unit 17. The cyclohexane in the second overhead stream 16 is converted to benzene and hydrogen in the dehydrogenation unit 17 and the resultant effluent stream 18 is recycled to the hydroalkylation reactor 11. Hydrogen, such as fresh make-up hydrogen, is optionally supplied to the dehydrogenation unit 17.

Figure 2:
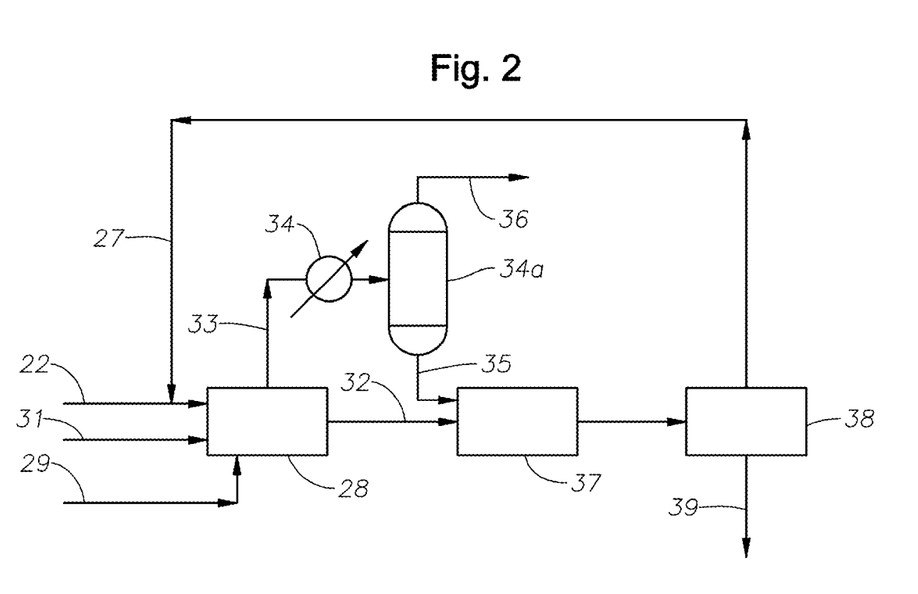
FIG. 2 is a flow diagram of the cyclohexylbenzene oxidation step of the process according to said one example of the invention.

A bottoms fraction 19 containing the desired cyclohexylbenzene together with some dicyclohexylbenzene is also recovered from the first distillation unit 13 and then passed to a second distillation unit 21, where the cyclohexylbenzene is removed as an overhead stream 22 for passage to the oxidation section shown in FIG. 2. A heavies purge stream 23 is also removed from the second distillation unit 21, together with an optional polyalkylate stream 24. When recovered, the polyalkylate stream 24 is fed to a transalkylation unit 25 together with part of the benzene-rich overhead stream 15 where the dicyclohexylbenzene in the stream 24 is transalkylated to produce additional cyclohexylbenzene. The effluent 26 from the transalkylation unit 25 is passed to the first distillation unit 13 for recovery of any unreacted benzene and subsequently of the cyclohexylbenzene as part of stream 22.

Referring now to FIG. 2, which is a flow diagram of the cyclohexylbenzene oxidation step of a preferred embodiment of the present process, the cyclohexylbenzene stream 22 recovered from the second distillation unit 21 is passed together with unreacted cyclohexylbenzene 27 recycled from downstream process steps to an oxidation reactor 28. The reactor 28 also receives oxidation catalyst 29 and an air stream 31, which oxidizes the cyclohexylbenzene in the presence of the catalyst 29 to produce a liquid product stream 32 composed mainly of cyclohexylbenzene hydroperoxide and unreacted cyclohexylbenzene and a flue gas stream 33 composed mainly of oxygen depleted air.

The flue gas stream 33 is fed to a condenser 34 where the majority of the organic materials in the stream 33 condense and separate from the non-condensible gas in the knock-out drum 34a as a liquid effluent stream 35. The remaining non-condensible gas exits the condenser as a vent gas stream 36 and is conveniently passed through an adsorbent bed (not shown), for example, activated carbon, for removal of additional organic materials before being vented from the system.

Figure 3:
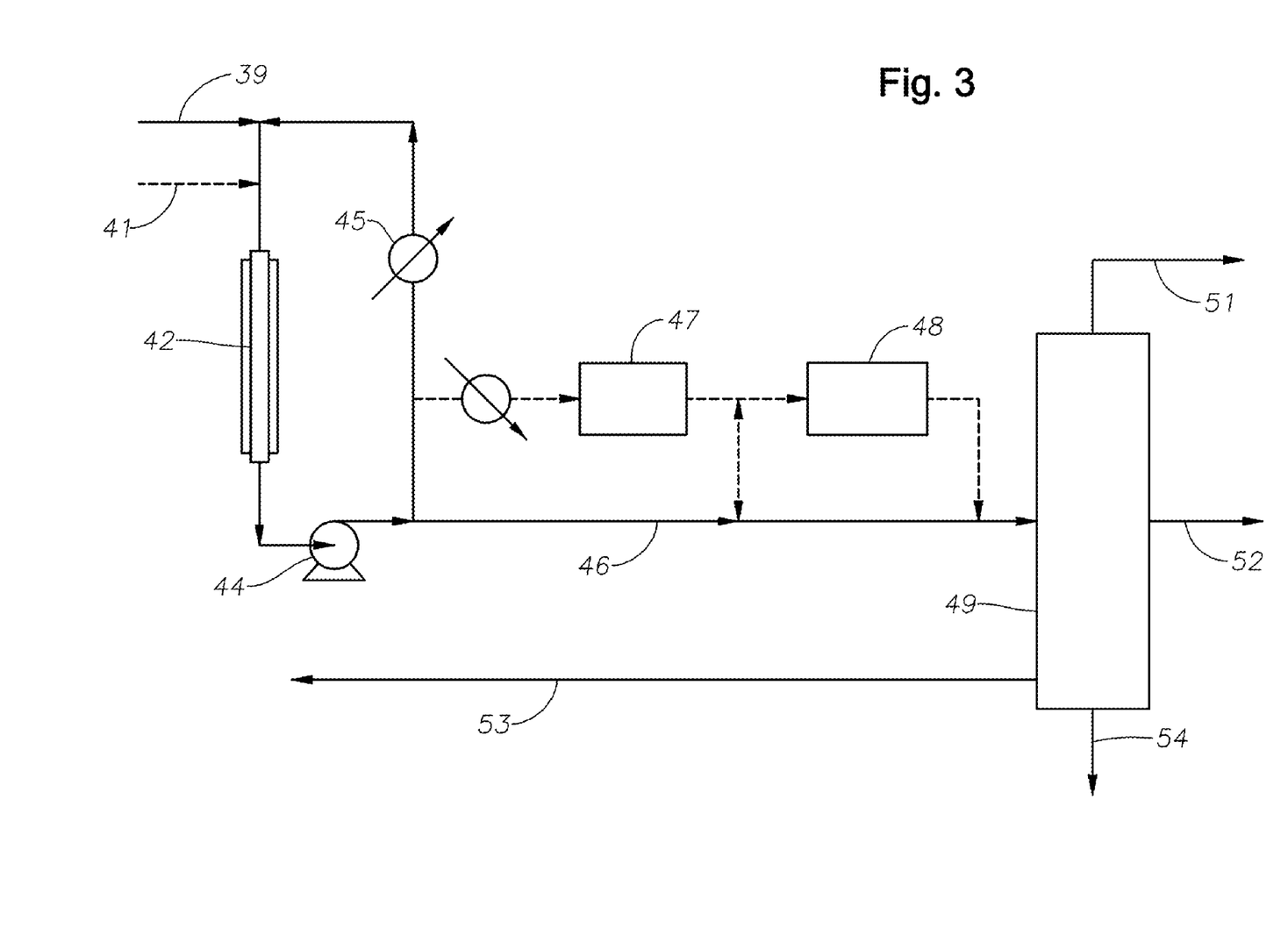
FIG. 3 is a flow diagram of the cyclohexylbenzene hydroperoxide cleavage and product recovery steps of the process according to said one example of the invention.

The liquid product stream 32 and the liquid effluent stream 35 are combined and may undergo an optional treatment step 37 and an optional concentration step 38 before being passed as stream 39 to the cleavage and product recovery section shown in FIG. 3. In the optional treatment step 37 the combined streams 32, 35 are treated to remove acids, such as organic acids produced as byproducts in the oxidation reactor 28 and phenolic acids present in the cyclohexylbenzene recycle stream(s). In the optional concentration step 38, at least a portion of the unreacted cyclohexylbenzene is stripped off in one or more vacuum flash/distillation steps so as to concentrate the cyclohexylbenzene hydroperoxide in the combined streams 32, 35. The unreacted cyclohexylbenzene 27 can then be recycled to the oxidation reactor 28.

Referring now to FIG. 3, which is a preferred embodiment of the cleavage process, the stream 39 composed mainly of cyclohexylbenzene hydroperoxide and unreacted cyclohexylbenzene is fed together with a sulfuric acid catalyst 41 to a cleavage reactor 42, shown as a tubular reactor provided with a circulating cooling system. The cooling system comprises a pump 44 which circulates the contents of the reactor 42 through a heat exchanger 45 so that the cooled reactor contents mix with and dilute the cyclohexylbenzene hydroperoxide in the stream 39 before the stream contacts the catalyst 41. In the reactor 42, the cyclohexylbenzene hydroperoxide is converted to phenol and cyclohexanone and so, as the reaction proceeds, the concentration of phenol and cyclohexanone builds up in the circulating reactor contents. Part of the reactor contents are therefore continuously removed as an effluent stream 46 for optional further treatment and for product recovery.

Further treatment of the cleavage reactor effluent 46 may optionally involve one or more further cleavage stages generally under more severe conditions that those used in the reactor 42. One such secondary cleavage reactor is shown at 47 in FIG. 3. Additional treatment of the cleavage reactor effluent 46 may involve treatment with a basic component, such as sodium phenylate, to neutralize the acid catalyst present in the effluent. One such neutralization step is shown at 48 in FIG. 3. In one embodiment, the optional secondary cleavage reactor(s) 47 and optional neutralization step(s) 48 may be combined in series.

After the optional treatment steps 47 and 48, the cleavage reactor effluent 46 is fed to a distillation system, which is shown generically at 49 but which would normally involve one or more extractive distillation units, where the effluent stream is divided into phenol and cyclohexanone product streams 51 and 52 respectively, an unreacted cyclohexylbenzene stream 53 and a heavies stream 54. The unreacted cyclohexylbenzene stream 53 is recycled to the oxidation reactor.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The invention claimed is:

1. A process for producing phenol and/or cyclohexanone, the process comprising:
    (a) contacting benzene and hydrogen with a first catalyst under hydroalkylation conditions to produce a first effluent stream comprising cyclohexylbenzene, cyclohexane, and unreacted benzene;
    (b) supplying at least part of said first effluent stream to a first separation system to divide said first effluent stream part into a cyclohexylbenzene-rich stream, a C6 product stream comprising cyclohexane and benzene;
    (c) contacting at least part of said C6 product stream with a second catalyst under dehydrogenation conditions to convert at least part of the cyclohexane to benzene and produce a second effluent stream comprising benzene and hydrogen;
    (d) recycling at least part of the second effluent stream to said contacting (a);
    (e) contacting at least part of said cyclohexylbenzene-rich stream with an oxygen-containing gas in the presence of a third catalyst under oxidation conditions to oxidize the cyclohexylbenzene in said cyclohexylbenzene-rich stream to produce cyclohexylbenzene hydroperoxide; and
    (f) converting cyclohexylbenzene hydroperoxide from (e) to produce phenol and cyclohexanone.

2. The process of claim 1 alternatively comprising:
    (g) dividing said C6 product stream in said supplying (b) into a cyclohexane-rich stream, and a benzene-rich stream;
    (h) recycling the benzene-rich stream to said contacting (a); and
    (i) contacting the cyclohexane-rich stream with a second catalyst in said contacting (c).

3. The process of claim 1, wherein the first catalyst comprises a molecular sieve and a hydrogenation metal.

4. The process of claim 3, wherein the molecular sieve of said first catalyst is selected from zeolite beta, zeolite X, zeolite Y, a MCM-22 family molecular sieve and mixtures thereof.

5. The process of claim 3, wherein the hydrogenation metal of said first catalyst is selected from palladium, ruthenium, nickel, zinc, tin, cobalt and mixtures thereof.

6. The process of claim 3, wherein at least 50 wt % of said hydrogenation metal is supported on an inorganic oxide different from said molecular sieve.

7. The process of claim 6, wherein said inorganic oxide comprises an oxide of at least one element of Groups 2, 4, 13 and 14 of the Periodic Table of Elements.

8. The process of claim 1, wherein said hydroalkylation conditions include a temperature of 50 to 400° C., a pressure of 100 to 7000 kPaa, a weight hourly space velocity of 0.01 to 100 hr$^{-1}$ and a benzene to hydrogen molar ratio of 0.01 to 100.

9. The process of claim 1 and further comprising dividing said first effluent stream into at least first and second portions; cooling the first portion of said first effluent stream; and recycling said cooled first effluent stream portion to said contacting (a).

10. The process of claim 1, wherein said dehydrogenation conditions comprise a temperature between 330° C. and 500° C. and a pressure between 100 and 1000 kPa.

11. The process of claim 1, wherein said second catalyst comprises a metal or compound thereof of Group 8 of the Periodic Table on a porous, non-acidic support.

12. The process of claim 1, wherein said third catalyst comprises a cyclic imide of the general formula (I):

wherein each of $R^1$ and $R^2$ is independently selected from hydrocarbyl and substituted hydrocarbyl radicals having 1 to 20 carbon atoms, or from the groups $SO_3H$, $NH_2$, OH, and $NO_2$ or from the atoms H, F, Cl, Br, and I, provided that $R^1$ and $R^2$ can be linked to one another via a covalent bond;

each of $Q^1$ and $Q^2$ is independently selected from C, CH, $CR^3$;

each of X and Z is independently selected from C, S, $CH_2$, N, P and elements of Group 4 of the Periodic Table;

Y is O or OH;

k is 0, 1, or 2;

l is 0, 1, or 2;

m is 1 to 3.

13. The process of claim 1, wherein said converting (f) is effected in at least two stages comprising a first stage conducted at a temperature of less than 50° C. and a second stage conducted at a temperature greater than the first stage temperature but less than 150° C.

14. The process of claim 1, wherein said converting (f) further comprises a third stage conducted at a temperature of 120° C. to 150° C.

15. The process of claim 1, wherein said converting (f) comprises contacting said cyclohexylbenzene hydroperoxide with a fourth catalyst, preferably sulfuric acid.

16. The process of claim 1 and further comprising converting at least part of the phenol produced in said converting (f) to further cyclohexanone or to a mixture of cyclohexanone and cyclohexanol.

17. The process of claim 1 and further comprising converting at least part of the cyclohexanone produced in said converting (f) to further phenol.

* * * * *